United States Patent
Albrecht et al.

(10) Patent No.: US 6,375,632 B1
(45) Date of Patent: Apr. 23, 2002

(54) JOINT SUPPORT WITH A GEAR WHEEL ADJUSTMENT MECHANISM FOR THE STEPLESS FINE ADJUSTMENT OF A PIVOT RANGE LIMIT

(75) Inventors: Erich Albrecht, Neubeuern; Hans-Georg Opahle, Rosenheim, both of (DE)

(73) Assignee: Albrecht GmbH (DE)

( * ) Notice: Subject to any disclaimer, the term of this patent is extended or adjusted under 35 U.S.C. 154(b) by 0 days.

(21) Appl. No.: 09/311,958

(22) Filed: May 14, 1999

(30) Foreign Application Priority Data

May 15, 1998 (DE) .......................... 198 21 950

(51) Int. Cl.$^7$ .................................. A61F 5/00
(52) U.S. Cl. .......................... 602/16; 602/26
(58) Field of Search ............ 602/16, 5, 19–21, 602/23, 26

(56) References Cited

U.S. PATENT DOCUMENTS

| | | | |
|---|---|---|---|
| 5,399,154 A | * 3/1995 | Kipnis et al. | ................ 602/26 |
| 5,421,810 A | * 6/1995 | Davis et al. | ............... 602/26 X |
| 5,437,619 A | * 8/1995 | Malewicz | ................. 602/16 X |
| 5,460,599 A | * 10/1995 | Davis et al. | .................. 602/26 |
| 5,885,235 A | 3/1999 | Opahle | |
| 5,938,629 A | * 8/1999 | Blodeau | ..................... 602/16 |
| 6,039,709 A | * 3/2000 | Bzoch | ....................... 602/16 X |

FOREIGN PATENT DOCUMENTS

| | | |
|---|---|---|
| AT | 393620 B | 11/1991 |
| DE | 19606092 | 2/1996 |

* cited by examiner

Primary Examiner—Denise Pothier
(74) Attorney, Agent, or Firm—Nixon & Vanderhye PC

(57) ABSTRACT

In the case of a joint support, and more particularly a knee joint support comprising an adjustment mechanism for an adjustment lever (24) limiting the pivot range of the distal splint (1) in relation to the proximal splint (2), the adjustment mechanism comprises a manually operated gear wheel drive with a drive gear wheel rotatably mounted on the distal splint (1), said drive gear wheel being in engagement with gearing provided on the adjustment lever (24).

7 Claims, 3 Drawing Sheets

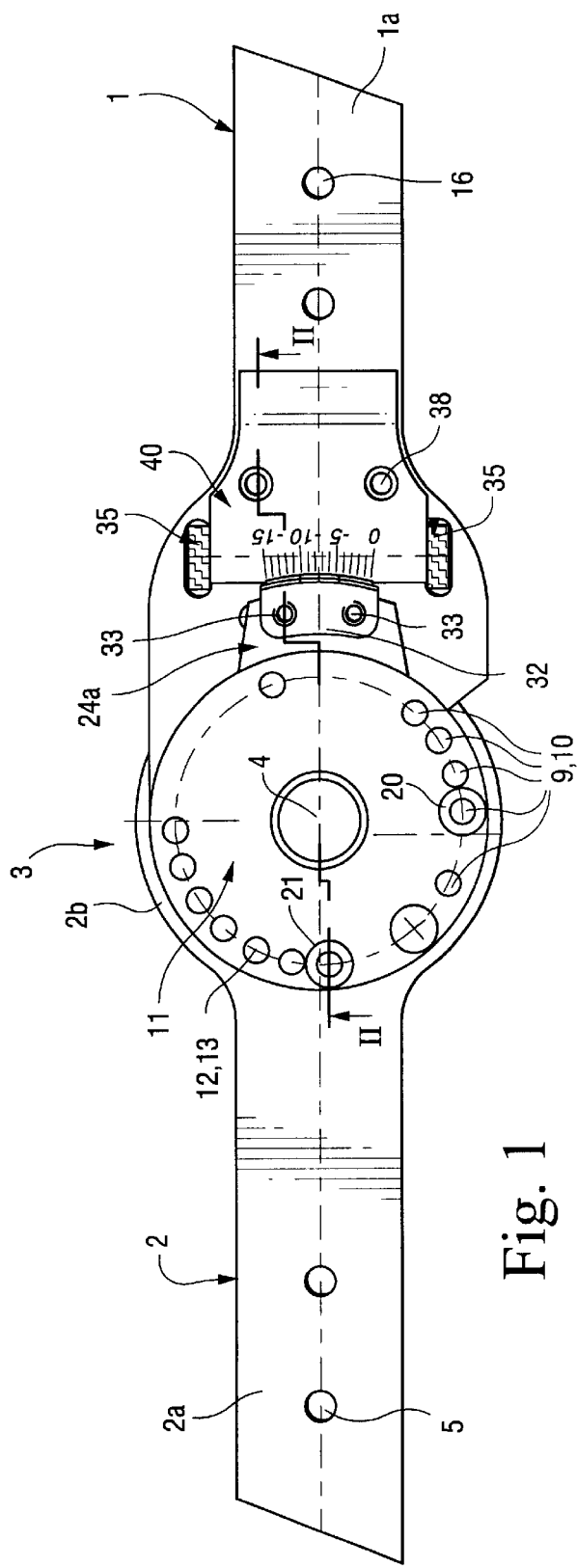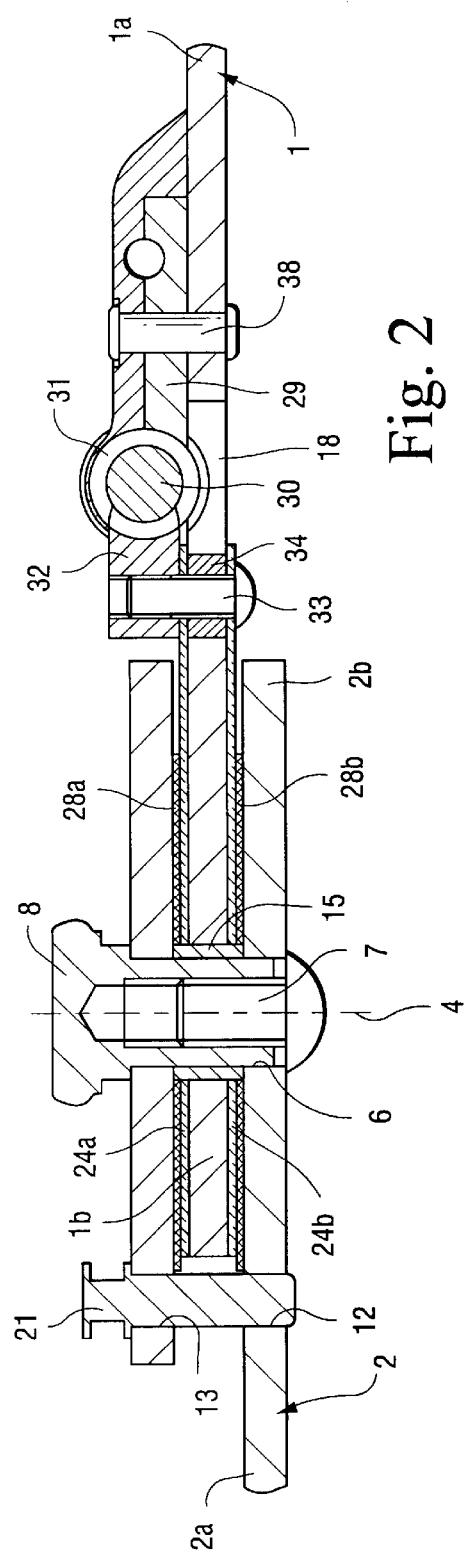

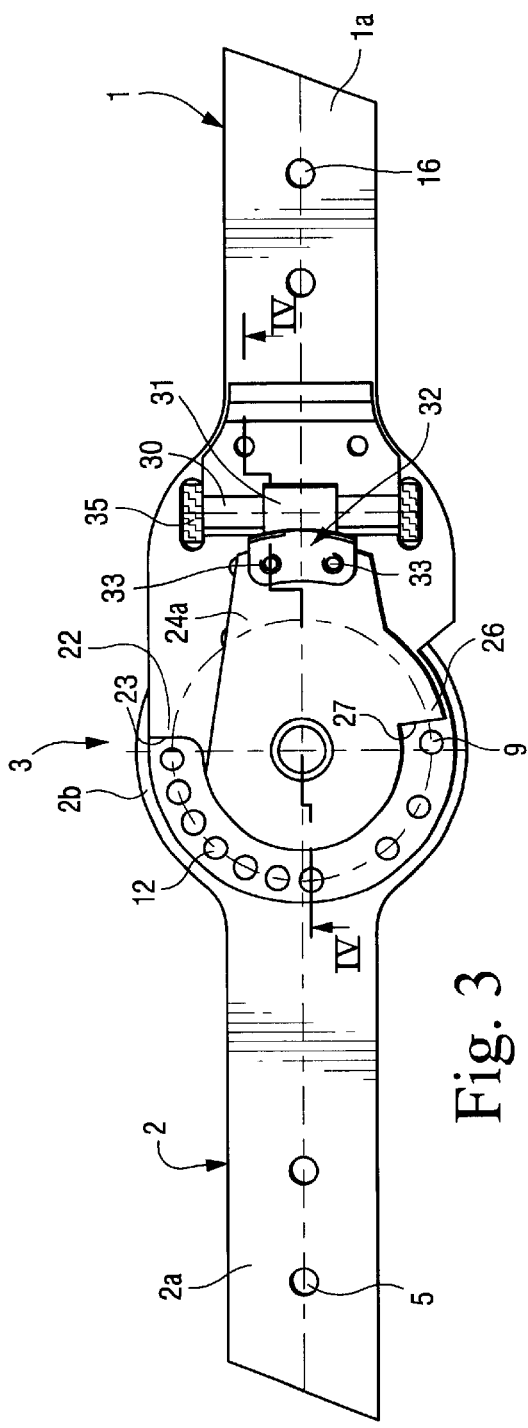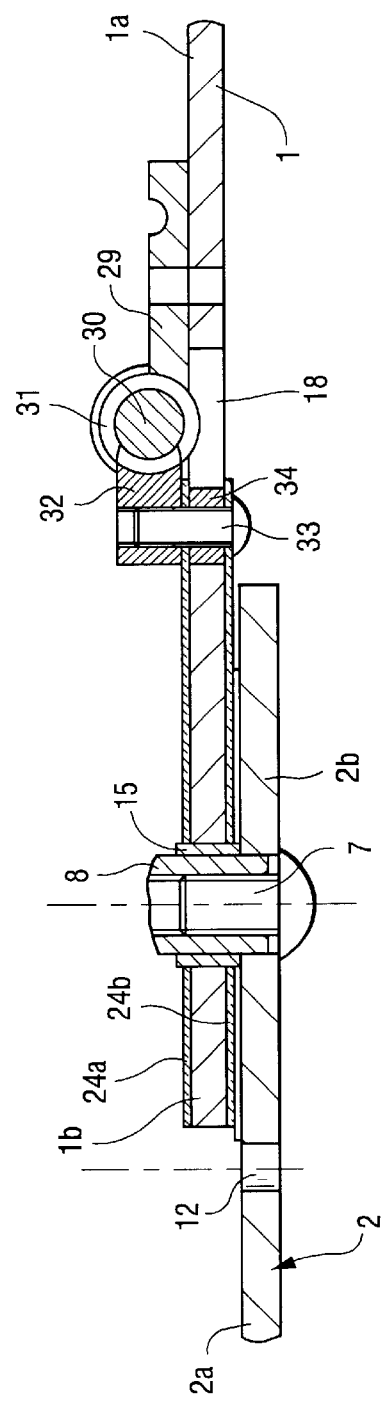

JOINT SUPPORT WITH A GEAR WHEEL ADJUSTMENT MECHANISM FOR THE STEPLESS FINE ADJUSTMENT OF A PIVOT RANGE LIMIT

BACKGROUND OF THE INVENTION

1. Field of the Invention

The invention relates to a joint support and more particularly, to a knee joint support with a gear wheel adjustment mechanism for limiting the pivot range of a distal splint in relation to a proximal splint.

2. Description of the Related Art

Joint supports of this type have been proposed as knee orthoses, which for instance are applied after cruciate ligament operations and permit a movement of the lower leg in relation to the upper leg under controlled conditions and furthermore stabilize the knee. The splints arranged on either side of the knee articulate together at the level of the knee joint and toward their free ends are strapped firmly on the upper and, respectively, lower leg. The pivotal joint in this respect permits flexing and extension of the leg for a predetermined range of pivoting which can be set.

The German patent publication 19,606,092 AI discloses a joint support of this type, in the case of which an adjustment lever, on which a counter-abutment is formed to limit the free range of pivoting, possesses a slot, which extends at a certain angle to a slot in the distal splint. A set screw extends through the two slots. By resetting the position of the set screw within the slots the adjustment lever and with it the counter-abutment can be pivoted about the pivot axis of the joint support with a high degree of precision and steplessly. In this respect it is possible to pivot the splint so far in the extension direction that an over-extension of the limb is ensured. Furthermore this arrangement ensures that the adjustment lever can be reliably fixed simply by somewhat doing up the set screw on the distal splint. This known joint support does in itself provide many advantages over other prior art joint supports, but does however entail using a tool in the form of an allen key for releasing and tightening the set screw. Such a tool is however not always to hand when the limit of the pivot range is to be reset.

Accordingly one object of the invention is to provide a joint support of the type initially mentioned, in the case of which setting of the adjustment lever in relation to the distal splint may be undertaken in the simplest possible fashion and without using a tool.

SUMMARY OF THE INVENTION

In the joint support of the invention the adjustment mechanism comprises a manually set gear wheel drive with a drive gear wheel mounted in a rotatable fashion on the distal splint and in engagement with gearing means on the adjustment lever.

With the aid of the adjustment mechanism of the invention the adjustment lever and accordingly the counter-abutment as well may be steplessly reset with the fingers and without having to employ any sort of tool. The limit to the range of pivoting, which is reached on abutment of the adjustment lever's counter-abutment against the abutment element on the proximal splint, may consequently be reset purely manually and steplessly within a certain angular range, as for instance within fifteen degrees.

It is convenient for the adjustment mechanism to comprise a self-locking gear drive and more especially in the form of a rotatable worm and by means of a worm wheel segment attached to the adjustment lever. By means of such a gear wheel drive the adjustment lever may be set with great precision and quite easily, such a gear wheel drive offering the further advantage of a self-locking action. This means that the load, which is applied by the limb to the splints, will not cause any loss of setting of the adjustment holding. Additional means to prevent for locking the gear wheel drive are hence unnecessary.

As an alternative to this it is however quite possible to utilize a other manually operated gear wheel drives instead of a worm and worm wheel drive and in the partial or total absence of a self-locking action to provide suitable catch members, which may be manually brought into and out of engagement with the gear wheel drive.

A particularly simple embodiment is one in which the driving drive part includes a shaft which is rotatably mounted on the distal splint to extend athwart the longitudinal axis of the distal splint, such shaft bearing the drive gear wheel, and more especially the worm. In at least one of its end parts, and preferably in both end parts, such a shaft may carry a knurled wheel which is able to be turned with the fingers to turn the drive gear wheel.

BRIEF DESCRIPTION OF THE DRAWINGS

The invention will now be described in the following with reference to the drawings by way of example.

FIG. 1 is a plan view of the joint support of the invention, the splints being shown to be somewhat shorter than is actually the case;

FIG. 2 is a section taken on the line II—II of FIG. 1 on a larger scale;

FIG. 3 is a plan view of the joint support in accordance with the invention without the indexing disk and without the bearing shell for the adjustment mechanism;

FIG. 4 is a section taken on the line IV—IV of FIG. 3 on a larger scale;

BRIEF DESCRIPTION OF THE PREFERRED EMBODIMENT

Figure 5:
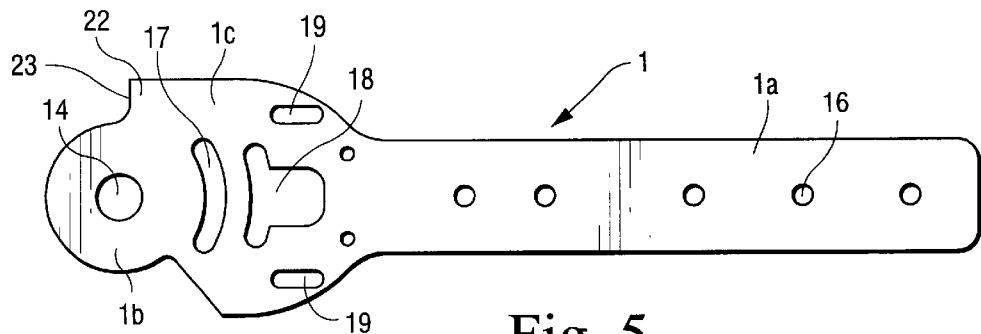
FIG. 5 is a plan view of a distal splint.

In the following, joint supports of the invention will be described with reference to FIGS. 1 through 12, which as a rule are employed in pairs of supports as illustrated, arranged on opposite sides of the joint and secured by means of straps, not illustrated, on the respective limbs, as for instance on the upper and lower leg. The joint support to be arranged on the opposite side of the joint is designed symmetrically with reference to the other support. The joint support in accordance with the invention will be described in the form of a knee orthosis, although it could find application for other joints, as for instance for the elbow joint.

As shown in FIGS. 1 through 4, the joint support of the invention comprises a distal splint 1, which may be secured to the lower leg using suitable straps, not illustrated, and a proximal splint 2, which may also be secured by means of suitable straps to the upper leg and is connected by means of a joint 3 with the distal splint 1. The pivot axis in this case referenced 4.

The proximal splint 2 possesses an elongated attachment portion 2a and a joint portion 2b in the form of a circular disk. In the attachment portion 2a several through holes 5 are provided for attachment of the straps, not illustrated.

The joint portion 2b in the form of a circular disk has a hole 6 in the center for the passage of a screw 7 and a holding sleeve 8, which are in the pivot axis 4. In the vicinity of the outer periphery five extension limiting holes 9 are furthermore provided, which are arranged in line with extension limiting holes 10 in an upper index disk 11, which defines a part of an abutment assembly. As shown in FIG. 1, four of the extension limiting holes 9 and 10 are here provided in the peripheral direction with an even spacing between them and respectively include an angle of 15 degrees.

On the other side of the central hole 6, seven flexion limiting holes 12 are provided in the joint section 2b of the proximal splint 2, such holes being axially aligned with seven flexion limiting holes 13 in the upper index disk 11. Mutually adjacent flexion limiting holes 12 are spaced apart by an angle of fifteen degrees.

Into the extension limiting holes 9 and 10 and the flexion limiting holes 12 and 13 it is possible for suitable abutment elements 20 and 21 to be plugged in order to limit the range of pivoting of the distal splint 1 in relation to the proximal splint 2 in the extension and flexion direction, as will be explained in more detail.

Between the joint section 2b of the proximal splint 2 and the upper index disk 11 there extends a joint section 1b of the distal splint 1 in parallelism thereto and at a distance therefrom, this joint section 1b being circular for somewhat more than half of its periphery. In the middle of the joint section 1b there is again a hole 14, through which the sleeve nut 8 or, respectively, a spacer sleeve 15, slipped over the sleeve nut 8, extends right through (FIGS. 2 and 4).

In a manner similar to that of the proximal splint 2, the distal splint 1 is able to be secured using an elongated attachment section 1a and straps, not illustrated, there being through holes in the attachment section 1a for threading the straps through.

Between the attachment section 1a and the joint section 1b of the distal splint 1 there is a widened transition section 1c, in which there is a circular slot 17, a recess 18 and two longitudinal recesses 19 (FIG. 5). The arcuate slot 17 and the recess 18 are in this respect arranged on the central longitudinal center line of the distal splint 1, whereas the longitudinal recesses 19 are located on opposite sides of the recess 18.

By means of an outwardly projecting spur 22 on the distal splint 1 an abutment face 23 is formed, which strikes against the abutment element 21 in order to limit the distal splint in the flexion direction.

Figure 6:
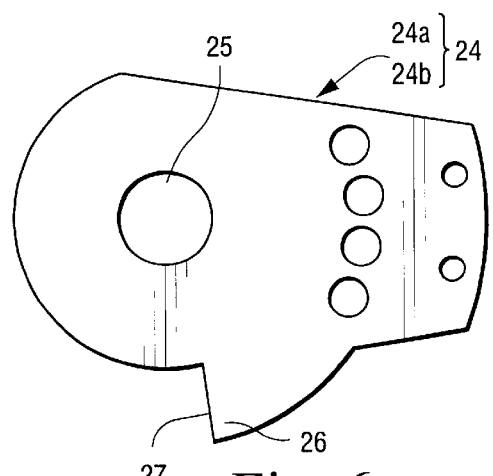
FIG. 6 is a plan view of an adjustment lever.
Figure 7:
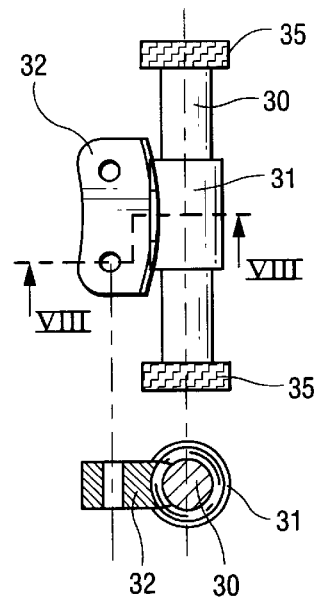
FIG. 7 is a plan view of the adjustment mechanism of the invention.
Figure 8:
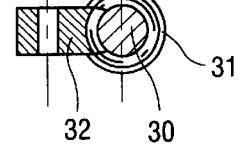
FIG. 8 is a section taken on the line VII—VII of FIG. 7.

As shown in the FIGS. 2 and 4 on the upper and lower side of the joint section 1b of the distal splint 1 there are respectively a sheet metal adjustment lever 24a and 24b, which are illustrated alone in FIG. 6. The two sheet metal adjustment levers 24a and 24b together constitute an adjustment lever 24, which may be pivoted in relation to the distal splint 1 about the pivot axis 4. For this purpose the sheet metal adjustment levers 24a and 24b possess a hole 25 through which the spacer sleeve 15 extends. A laterally projecting spur forms a counter abutment 26 with an abutment face 27. The abutment face 27 strikes against the abutment element 20, when the distal splint 1 is pivoted to the maximum degree in the extension direction.

As is furthermore shown in FIG. 2 between the upper sheet metal adjustment holding 24a and the index disk 11 and between the lower sheet metal adjustment lever 24b and the joint section 2b of the proximal splint 2 there is respectively a friction reducing disk 28a and, respectively, 28b, for instance in the form of thin Teflon disks or washers.

Owing to the different arrangements, together with the adjustment lever 24 the distal splint 1 can be pivoted about the axis 4 in relation to the proximal splint 2 and the index disk 11. The pivot movement in the flexion direction is set by the position at which the abutment face 23 on the distal splint 1 strikes the abutment element 21 and may be reset in steps of 15° by replugging the abutment element 21 in different flexion limiting holes 12 and 13. The pivot motion in the extension direction is limited by the position at which the abutment face 27 strikes against the sheet metal adjustment levers 24a and 24b on the abutment element 20 and may be changed by replugging the abutment element 20 in different extension limiting holes 9 and 10 in 15° angular steps.

In addition to this stepped variation of the pivot range limit in the extension direction it is possible in the case of the illustrated working embodiment to perform a stepless modification of the pivot range limit in the extension direction by pivoting the sheet metal adjustment levers 24a and 24b in relation to the distal splint 1.

For this purpose an adjustment mechanism of the worm and worm wheel type is provided. This adjustment mechanism comprises, as indicated in FIGS. 1 through 4 and FIGS. 7 and 8, a shaft 30 rotatably mounted in a lower bearing shell 29 in the distal splint 1 and extending transversely in relation to the longitudinal direction of the distal splint, such shaft bearing a gear 31 (hereinafter referred to as worm 31) in the middle thereof. This worm 31 is an engagement with a gear wheel segment 32 (hereinafter referred to as worm wheel segment 32), which is attached to the distal end of the sheet metal adjustment levers 24a and 24b by means of two screws 33. The worm wheel segment 32 is in this case located radially clear of the index disk 11 and is seated on the upper sheet metal adjustment lever 24a. In order to ensure that the two sheet metal adjustment levers 24a and 24b are not compressed and deformed by the screws 33 a spacer sleeve 34 is provided between them. Rotation of the worm 31 is performed manually by means of two knurled wheels 35, which are provided in the two end parts of the shaft. If the worm 31 is rotated, the worm wheel segment 32 and with the two sheet metal adjustment levers 24a and 24b will move in relation to the distal splint 1 about the pivot axis 4.

The screw 33 and, respectively, the spacer sleeve 34 are located in this case operatively adjacent to the recess 18 in the distal splint 1 so that such parts may move within the recess 18. Furthermore, the worm 31 as well extends partially into the recess 18 so that the worm 31 and with it the shaft 30 may not be shifted transversely in relation to the longitudinal direction of the distal splint 1. The knurled wheels 35 fit into the longitudinal recesses 19 in the distal splint 1 so that a lower overall height is ensured.

Figure 9:
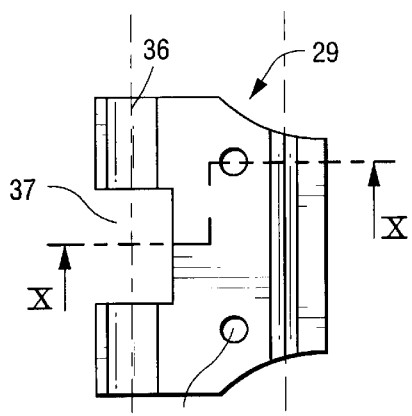
FIG. 9 is a plan view of the lower bearing shell of the adjustment mechanism.
Figure 10:
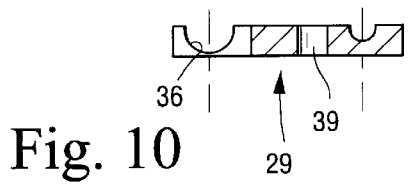
FIG. 10 is a section taken on the line X—X of FIG. 9.

The lower bearing shell 29 illustrated in more detail in FIGS. 9 and 10 is best manufactured in the form of a flat, plate-like plastic component, in which from above a transverse groove 36, extending over the full width of the bearing shell 29, is produced having a semicircular cross section. In this transverse groove 36 the shaft 30 is mounted. By having a middle recess 37 the free space required for the worm 31 is created in the downward direction. The attachment of the lower bearing shell 29 is performed in the illustrated working embodiment using rivets 38 (FIG. 2), which extend through suitable holes 39 in the lower bearing shell 29.

Figure 11:
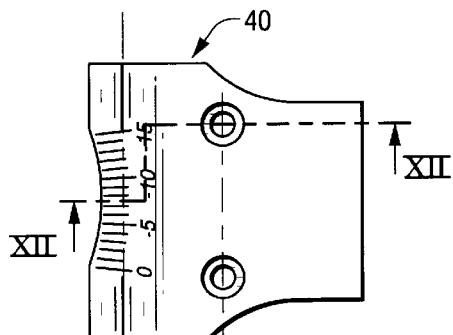
FIG. 11 is a plan view of the upper bearing shell of the adjustment mechanism.
Figure 12:
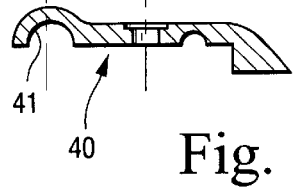
FIG. 12 is a plan view taken on the line XII—XII of FIG. 10.

In order to hold the shaft 30 in the upward direction, a lower bearing shell 40 is provided, which is illustrated in a separate view in FIGS. 11 and 12. The upper bearing shell 40 overlaps the lower bearing shell 29 and the shaft 30 with the worm 31 completely and is also held by means of the rivets 38 in the lower bearing shell 29. A curved transverse groove corresponding to the transverse groove 36 but having the opposite direction of curvature and with a semicircular cross section rests on the shaft 30 and/or the worm 31 to prevent upward movement thereof. Furthermore as shown in FIGS. 1 and 11 a scale is provided on the top side of the top bearing shell 40, such scale having an angular range of 0 to 15° and rendering possible accurate reading of the relative position of the worm wheel segment 32 and consequently of the sheet metal adjustment levers 24a and 24b in relation to the distal splint 1. If the extension abutment element 20 is in the 0° extension limiting hole 9 and 10, then by adjustment of the sheet metal adjustment levers 24a and 24b the distal splint 1 may be pivoted steplessly as far as an over-stretch of −15° in relation to the proximal splint 2.

While the invention has been described in connection with a preferred embodiment, it will be apparent to those skilled in the art that many changes and modifications may be made without departing from the true spirit and scope of the present invention. Accordingly, it is intended by the appended claims to cover all such changes and modifications as come within the spirit and scope of the invention.

What is claimed is:

1. A support for a joint of a human limb comprising:

a distal splint member configured to be attached to a distal portion of said limb;

a proximal splint member configured to be attached to a proximal portion of said limb;

said distal and proximal splint members being pivotably connected for relative movement about a pivot axis;

an abutment assembly coupled to said proximal splint member at a position disposed proximate said pivot axis;

an adjustment lever pivotably mounted for movement about said pivot axis and having a counter-abutment portion for cooperating with said abutment assembly; and an adjustment mechanism provided on said distal splint member in engagement with said adjustment lever for adjusting the rotational position of said adjustment lever through a continuous predetermined angular range of rotation about said pivot axis;

wherein said adjustment mechanism comprises a gear rotatably mounted on the distal splint member, said gear being in engagement with a gear wheel provided on said adjustment lever, and wherein said abutment assembly includes at least one adjustable abutment element so that a range of pivoting of the distal splint in relation to the proximal splint in at least one of an extension and flexion direction can be selectively determined, wherein said abutment assembly comprises a disk mounted coaxially to said pivot axis, said at least one adjustable abutment element being coupled to said disk.

2. The support of claim 1 wherein the gear of the adjustment mechanism and the gear wheel of said adjustment lever are self-locking.

3. The support of claim 1 wherein said gear is supported by a shaft extending transversely in relation to a longitudinal axis of said distal splint member.

4. The support of claim 3 wherein said shaft is provided with at least one manually engageable end portion for manually rotating said gear.

5. The support of claim 1 wherein said gear wheel provided on said adjustment lever is arranged to face in a direction of a free end on said distal splint member.

6. The support of claim 1 wherein said gear is a worm structure and said gear wheel of the adjustment lever is a worm wheel segment.

7. A support as in claim 1, wherein a plurality of flexion limiting openings are defined in said disk for selectively receiving said at least one adjustable abutment element.

* * * * *